US010159796B2

(12) United States Patent
Schiff et al.

(10) Patent No.: US 10,159,796 B2
(45) Date of Patent: Dec. 25, 2018

(54) SYRINGE ASSEMBLY HAVING A TELESCOPING PLUNGER ROD

(71) Applicant: Becton Dickinson France, S.A.S., Le Pont-de-Claix (FR)

(72) Inventors: David Robert Schiff, Highland Park, NJ (US); Mathieu Dominic Turpault, Pennington, NJ (US); Antonio Gatta, Philadelphia, PA (US); John Depler Coleman, Philadelphia, PA (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 1169 days.

(21) Appl. No.: 13/622,384

(22) Filed: Sep. 19, 2012

(65) Prior Publication Data
US 2013/0082057 A1 Apr. 4, 2013

Related U.S. Application Data

(60) Provisional application No. 61/541,658, filed on Sep. 30, 2011.

(51) Int. Cl.
*A61M 5/315* (2006.01)
*A61M 5/31* (2006.01)
(Continued)

(52) U.S. Cl.
CPC ......... *A61M 5/31511* (2013.01); *A61M 5/002* (2013.01); *A61M 5/5086* (2013.01);
(Continued)

(58) Field of Classification Search
CPC .............. A61M 5/31511; A61M 5/002; A61M 5/5086; A61M 2005/3104; A61M 2005/31518
See application file for complete search history.

(56) References Cited

U.S. PATENT DOCUMENTS 5,722,951 A * 3/1998 Marano ............... A61M 5/5066
604/110
6,905,478 B2 * 6/2005 Ingram ............. A61M 5/31501
604/110

(Continued)

FOREIGN PATENT DOCUMENTS

WO 2009/108847 A1 9/2009

*Primary Examiner* — Lauren P Farrar
(74) *Attorney, Agent, or Firm* — The Webb Law Firm

(57) ABSTRACT

A syringe assembly including a syringe barrel having a first end, a second end, and a sidewall extending therebetween defining a chamber is disclosed. The syringe assembly includes a stopper disposed within the chamber of the syringe barrel and a plunger rod having an inner member engaged with the stopper and an outer member adapted for telescopic movement with respect to the inner member. The plunger rod is transitionable from a collapsed position, in which a portion of the inner member is nested within the outer member, to an extended position, in which the same portion of the inner member extends outside the outer member. The syringe assembly also includes a stop member configured for cooperation with a portion of the syringe barrel, upon relative movement of the outer member with respect to the inner member, to limit the outward travel of the plunger rod from the syringe barrel.

17 Claims, 15 Drawing Sheets

(51) Int. Cl.
    *A61M 5/50*     (2006.01)
    *A61M 5/00*     (2006.01)

(52) U.S. Cl.
    CPC ............... *A61M 2005/3104* (2013.01); *A61M 2005/31518* (2013.01)

(56) References Cited

U.S. PATENT DOCUMENTS

| | | | |
|---|---|---|---|
| 2004/0092884 A1* | 5/2004 | Rimlinger | A61M 5/326 604/198 |
| 2007/0017533 A1* | 1/2007 | Wyrick | A61M 5/2033 128/898 |
| 2009/0259195 A1* | 10/2009 | Lin Lee | A61M 5/24 604/195 |
| 2009/0318880 A1* | 12/2009 | Janish | A61M 5/31511 604/228 |
| 2013/0085452 A1 | 4/2013 | Schiff et al. | |
| 2013/0085457 A1 | 4/2013 | Schiff et al. | |

* cited by examiner

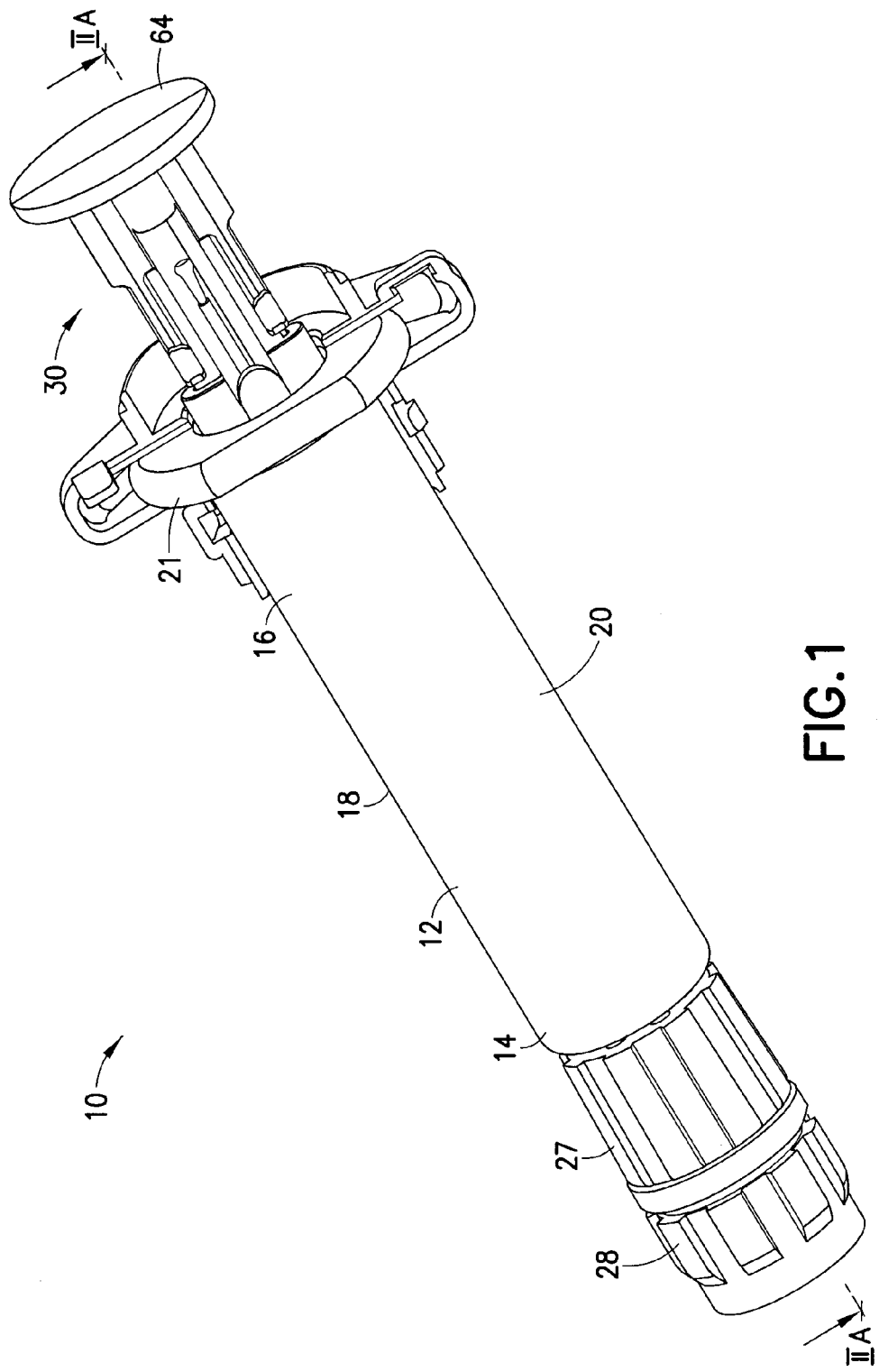

SYRINGE ASSEMBLY HAVING A TELESCOPING PLUNGER ROD

CROSS-REFERENCE TO RELATED APPLICATION

This application claims priority to U.S. Provisional Application Ser. No. 61/541,658 filed Sep. 30, 2011, the entire disclosure of which is hereby incorporated by reference.

BACKGROUND OF THE INVENTION

Field of the Invention

The present invention is directed to a pre-filled syringe assembly adapted for the dispensing and delivery of a fluid. More particularly, the present invention is directed to a pre-filled syringe assembly having a telescopic plunger rod having a pull-out safety arrangement wherein the plunger rod arrangement results in a smaller packaging footprint allowing for reduced storage space. The present invention is also directed to a packaging system for a pre-filled syringe assembly that prevents unintended actuation of the plunger rod and reduces the likelihood of tampering of the syringe contents.

Description of Related Art

Conventional syringes are well known to be used in connection with a vial of a medication, wherein the user draws the fluid into the syringe immediately prior to injection and delivery of the fluid to the patient. A conventional syringe typically includes a syringe barrel with an opening at one end and a plunger mechanism disposed through the other end. The plunger mechanism typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery. Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing this syringe. It is also desirable to produce syringes that are uniform in terms of an outer surface shape to allow for stacking of the syringes within the storage cabinet.

Even though measures, such as controlled storage, are taken to ensure the contents of these syringes remain intact, the risk still remains that the syringe contents can be tampered with and/or stolen and replaced with a saline solution. One technique for preventing tampering is the use of a snap cap for the tip cap that makes a snapping noise when removed from the syringe assembly. Conventional tamper-proof caps for pre-filled syringes may include a top member concentrically disposed in a generally cylindrical sleeve member and connected by frangible elements to the sleeve member. Conventional outer caps for pre-filled syringes cover a cylindrical cover cap which connects with the top wall of a holding member through a frangible portion. The cylindrical cover cap may be broken from the top wall of the holding member for tampering prevention/tamper-proof evidence.

SUMMARY OF THE INVENTION

In accordance with an embodiment of the present invention, a syringe assembly includes a syringe barrel having a first end, a second end, and a sidewall extending between the first end and the second end defining a chamber. The syringe assembly also includes a stopper disposed within the chamber of the syringe barrel and a plunger rod engaged with the stopper. The plunger rod has an inner member including a distal end secured to the stopper and an outer member adapted for telescopic movement with respect to the inner member. The plunger rod is transitionable from a collapsed position, in which a portion of the inner member is nested within the outer member, to an extended position, in which the same portion of the inner member extends outside the outer member. The syringe assembly further includes at least one stop member configured for cooperation with a portion of the syringe barrel upon relative movement of the outer member with respect to the inner member to limit the outward travel of the plunger rod from the syringe barrel. The stop member limits pull-out of the plunger rod from the syringe barrel, i.e., wherein too much proximal force is applied to the plunger rod to inadvertently remove the plunger rod from the syringe barrel. The syringe assembly can be of a pre-filled type including a medication or drug disposed within the syringe barrel.

In certain configurations, the stop member can comprise a laterally extending member positioned at the distal end of the inner member. This laterally extending member is configured to cooperate with an internal portion of a syringe barrel flange to limit the outward travel of the plunger rod from the syringe assembly upon extension of the plunger rod to the ready-to-use position. The inner member can include a locking member for cooperating with an aperture in the outer member for locking the outer member to the inner member in the extended position. The outer member can include a pair of holding members surrounding the aperture and the locking member can include a pair of reverse bevels for cooperating with the pair of holding members to maintain the outer member in the extended position upon the application of a distal and/or a proximal force applied to the outer member. According to one design, the inner member can include a substantially X-shaped profile configured for engagement with a corresponding substantially X-shaped opening within the outer member.

The syringe can also include at least one detent associated with the outer member which is configured to cooperate with the syringe barrel to limit movement of the outer member into the syringe barrel upon the application of a distally directed force to the plunger rod. This particular feature would prevent the application of a partial dose of a pre-filled syringe, should a distal force be applied to the plunger rod prior to extension of the outer member.

According to another configuration, the stop member can comprise at least one longitudinally extending arm associated with the outer member wherein the longitudinally extending arm extends along an outer portion of the syringe barrel. The at least one longitudinally extending arm can include an inwardly extending detent at one end thereof configured for contacting an outer flange of the syringe barrel when the outer member is in the extended ready-to-use position, for limiting the outward travel of the outer member. According to one design, the at least one longitudinally extending arm can comprise a pair of arms, each of the arms including the inwardly extending detent at one end thereof configured for contacting the outer flange of the syringe barrel. In this configuration, the syringe barrel can include at least one pocket for enclosing the at least one longitudinally extending arm when the outer member is in the collapsed position, and the at least one pocket cooperates with the outer flange of the syringe barrel to position and hold the detent in contact with the outer flange.

The syringe assembly can include a molded cover having a tear tab for removal of the cover. This cover can be of a design that is configured to constrain the plunger rod from inadvertent transition to the extended position.

In accordance with another embodiment of the present invention, a telescopic plunger rod assembly for use with a syringe assembly includes an inner member having a distal end configured for being secured to a stopper located within a syringe barrel, and an outer member having an open portion configured for telescopically engaging a portion of the inner member. The plunger rod is transitionable from a collapsed position to an extended position. The plunger rod includes at least one stop member configured for cooperation with a portion of the syringe barrel to limit the outward travel of the outer member from the syringe barrel upon transition of the plunger rod to the extended position.

In certain configurations, the stop member can comprise a laterally extending member positioned at the distal end of the inner member and configured to cooperate with an internal portion of a syringe barrel flange to limit the outward travel of the plunger rod from the syringe assembly upon extension of the plunger rod to the ready-to-use position. The inner member can include a locking member configured for cooperating with an aperture in the outer member for locking the outer member to the inner member in the extended position. According to one design, the inner member can include a substantially X-shaped profile configured for engagement with a corresponding substantially X-shaped opening within the outer member. At least one detent can be associated with an outer sleeve and configured to: cooperate with the syringe barrel to limit movement of the outer sleeve into the syringe barrel upon the application of the distally directed force to the plunger rod; and prevent the application of a partial dose of the syringe contents.

According to another configuration, the stop member can comprise a pair of longitudinally extending arms associated with the outer member wherein the longitudinally extending arms extend along an outer portion of the syringe barrel. The longitudinally extending arms can include an inwardly extending detent configured for contacting an outer flange of the syringe barrel when the outer member is in the extended ready-to-use position.

In accordance with another embodiment of the present invention, a packaging assembly for use with a pre-filled syringe assembly includes a molded cover configured for placement about a portion of a syringe barrel, a plunger rod, and a tip cap and a tear tab associated with one end of the molded cover. The tear tab is configured to facilitate removal of the molded cover from the syringe assembly and can be positioned adjacent a top surface of the plunger rod. The cover is configured for placement about the syringe assembly, including the tip cap, to constrain the plunger rod from inadvertent transition to the extended position.

BRIEF DESCRIPTION OF THE DRAWINGS

FIG. 1 is a front perspective view of a syringe assembly having a telescopic plunger rod in a collapsed position in accordance with an embodiment of the present invention.

DESCRIPTION OF THE PREFERRED EMBODIMENTS

Figure 1A:
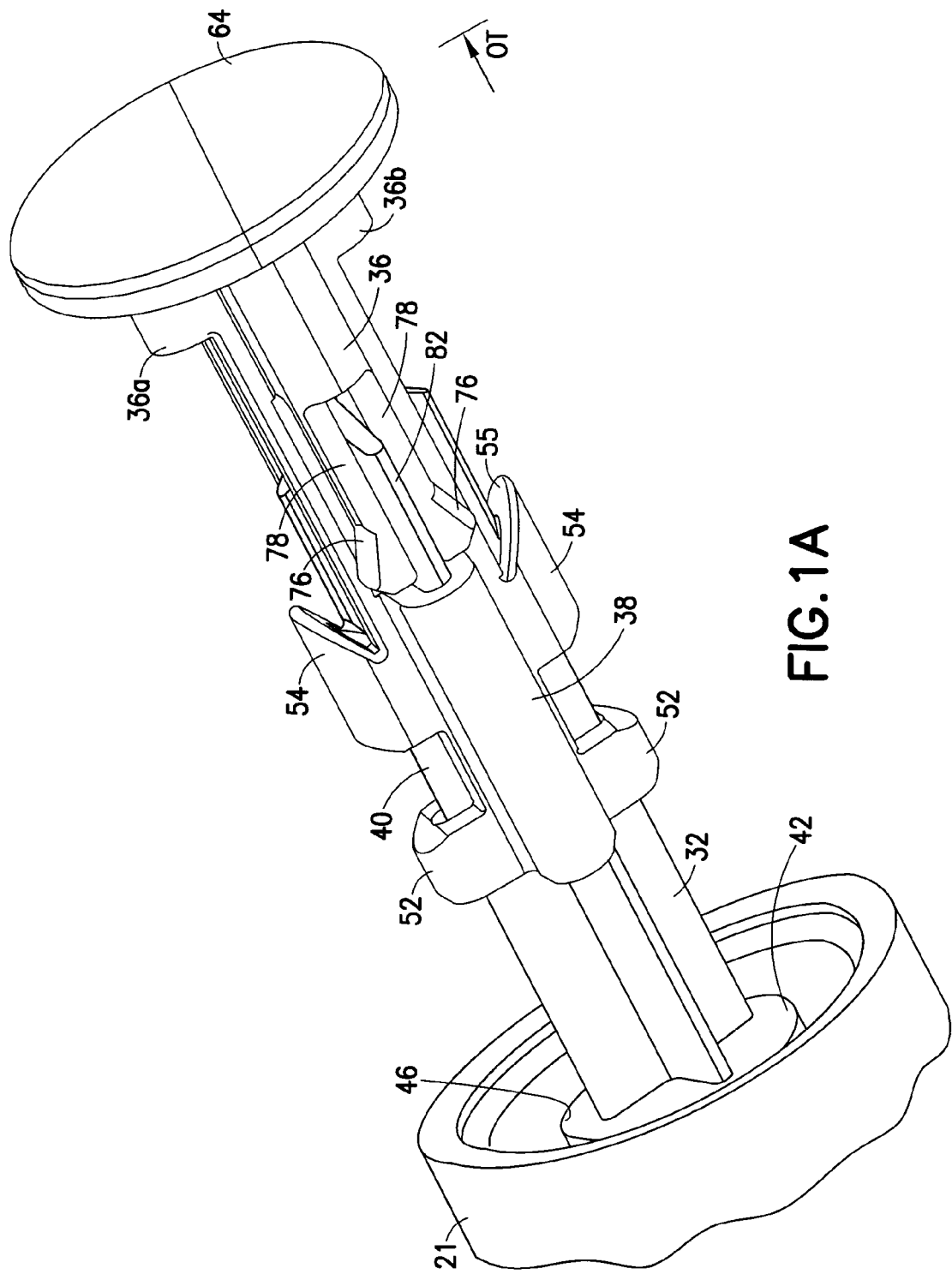
FIG. 1A is a front perspective view of the telescopic plunger rod of the syringe assembly of FIG. 1 with the plunger rod in an extended position in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1, 1A-1B, 2A-2B, 3, 4A-4B, and 5A-5B, which depict a syringe assembly according to an embodiment of the present invention, generally indicated as 10, adapted for the dispensing and delivery of a fluid. FIGS. 6A-6B and 7A-7B depict a syringe assembly according to a further embodiment of the invention, generally indicated as 100, which can also be adapted for the dispensing and delivery of a fluid. FIGS. 8A-8C depict a packaging assembly, generally indicated as 200, and the operational steps for removing the packaging assembly, which can be used for packaging the syringe assembly of the invention.

With particular reference to FIGS. 1, 2A-2B, and 3, the syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 12 having a first or distal end 14, a second or proximal end 16, and a sidewall 18 extending between the distal end 14 and proximal end 16 defining an interior chamber 20 of the syringe barrel 12. A stopper 22 is slidably disposed within the chamber 20 of the syringe barrel 12. The syringe barrel 12 may be in the general form of an elongated cylindrical barrel as is known in the art for the general shape of a hypodermic syringe, although other forms for containing a fluid for delivery are also contemplated by the present invention. Additionally, the syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include an outwardly extending flange 21 about at least a portion of the proximal end 16. The flange 21 may be configured for easy grasping by a medical practitioner, as will be discussed herein.

Figure 3:
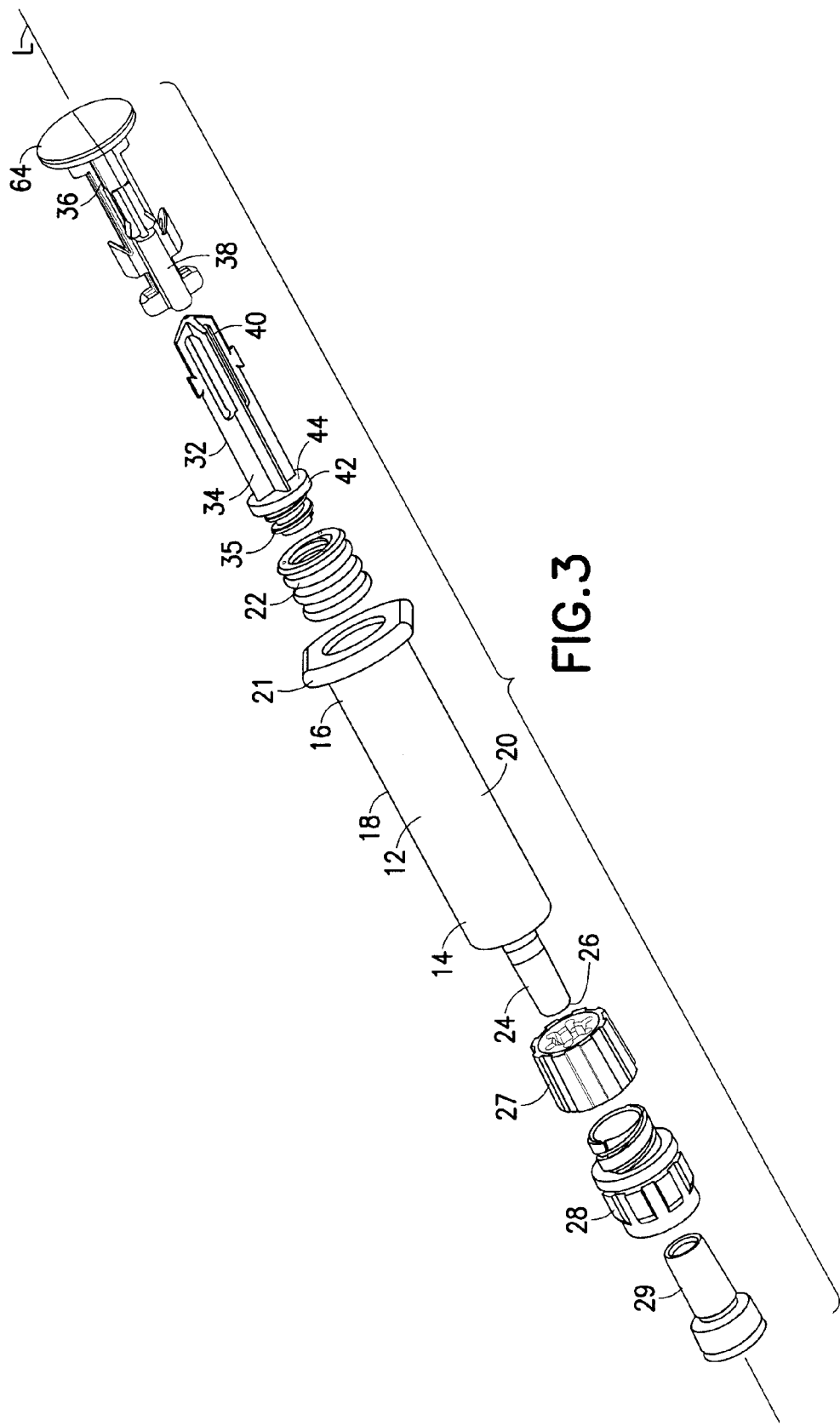
FIG. 3 is an expanded perspective view of the syringe assembly of FIG. 1 in accordance with an embodiment of the present invention.
Figure 4A:
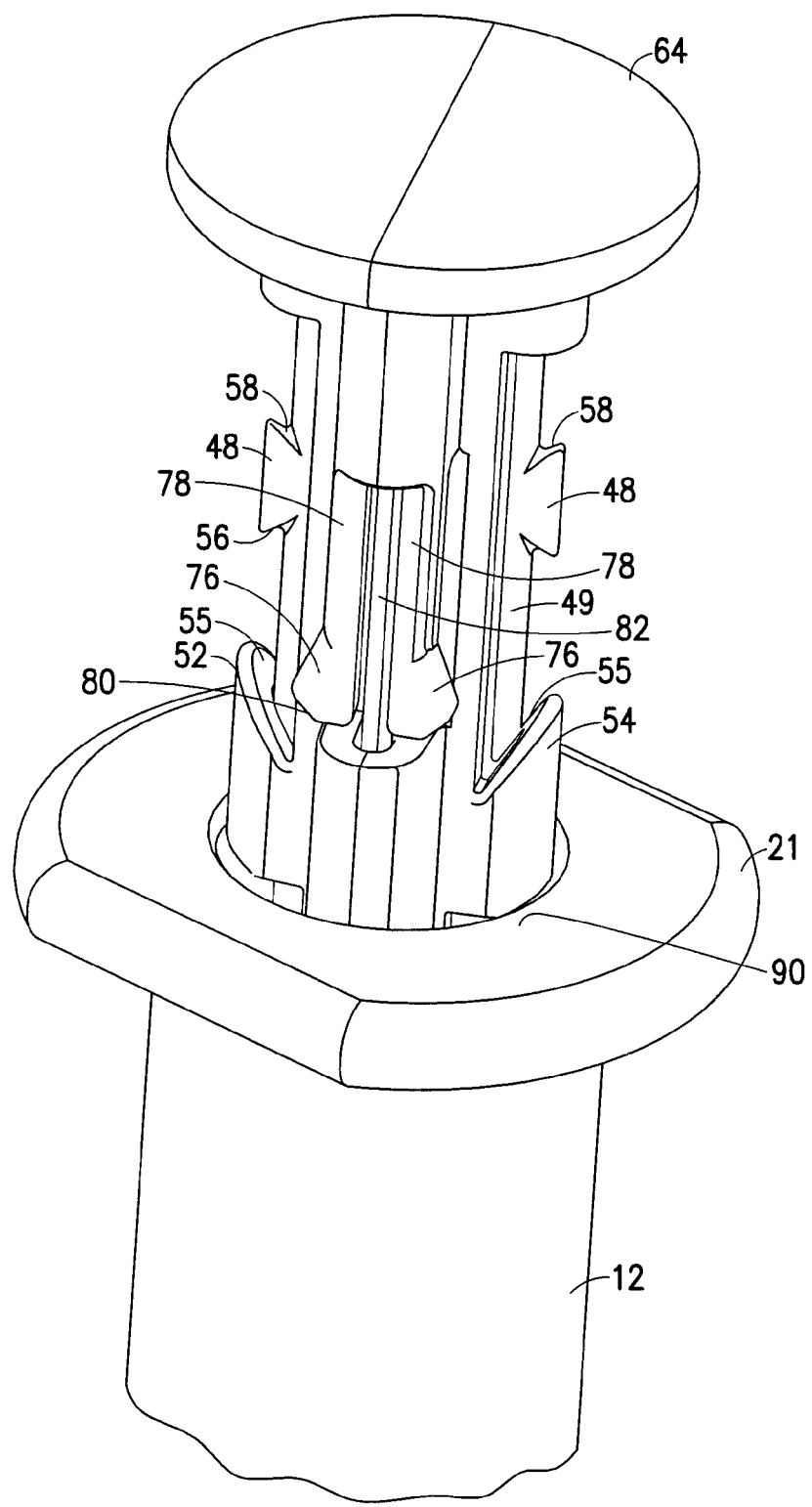
FIG. 4A is a front perspective view of the plunger rod assembly of the syringe assembly of FIG. 1 in the collapsed position including the partial dose feature in accordance with an embodiment of the present invention.
Figure 4B:
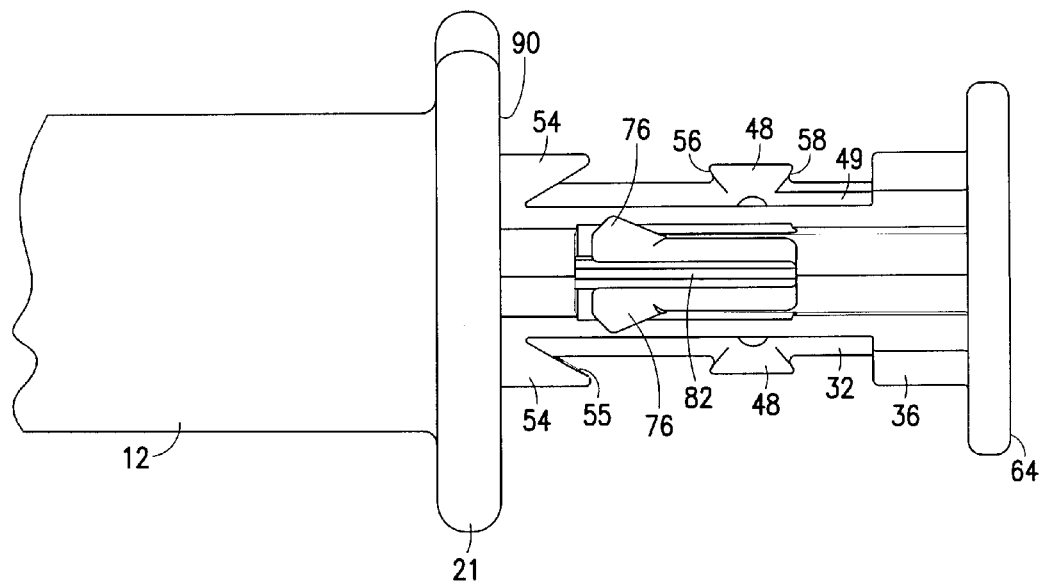
FIG. 4B is a side elevation view of the plunger rod assembly of the syringe assembly of FIG. 4A in accordance with an embodiment of the present invention.

As illustrated in FIG. 3, the distal end 14 of the syringe barrel 12 terminates in a tip 24 having an outlet opening 26. The proximal end 16 is generally open-ended, but is intended to be closed off to the external environment, via the stopper 22, as will be discussed herein. According to one non-limiting embodiment, as shown in FIG. 3, the syringe assembly 10 can include a tip cap 28, an interface member 27 interfacing between the tip cap 28 and the tip 24 of the syringe barrel 12, and a plug 29, for sealing the outlet opening 26.

The syringe barrel 12 may include markings, such as graduations on the sidewall 18 thereof, for providing an indication as to the level or amount of fluid contained within the syringe barrel 12. Such markings may be provided on the external wall, the internal wall, or integrally formed or otherwise within the wall of syringe barrel 12. Alternatively, or in addition thereto, the markings may provide a description of the contents of the syringe, or other identifying information, as may be known in the art.

As noted, distal end 14 of syringe barrel 12 includes an outlet opening 26. The profile of outlet opening 26 may be adapted for engagement with a separate dispensing device, such as a needle assembly or IV connection assembly, and therefore may include a mechanism for such engagement, for example, a generally tapered luer tip, for engagement with a separate tapered luer mating surface (not shown) of such a separate device for attachment therewith. In addition, a mechanism for locking engagement therebetween may also be provided, such as a luer collar or luer lock including interior threads. Such luer connections and luer locking mechanisms are well known in the art.

All of the components of syringe assembly 10 may be constructed of any known material, and are desirably constructed of medical grade polymers. As stated above, the syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

Figure 1B:
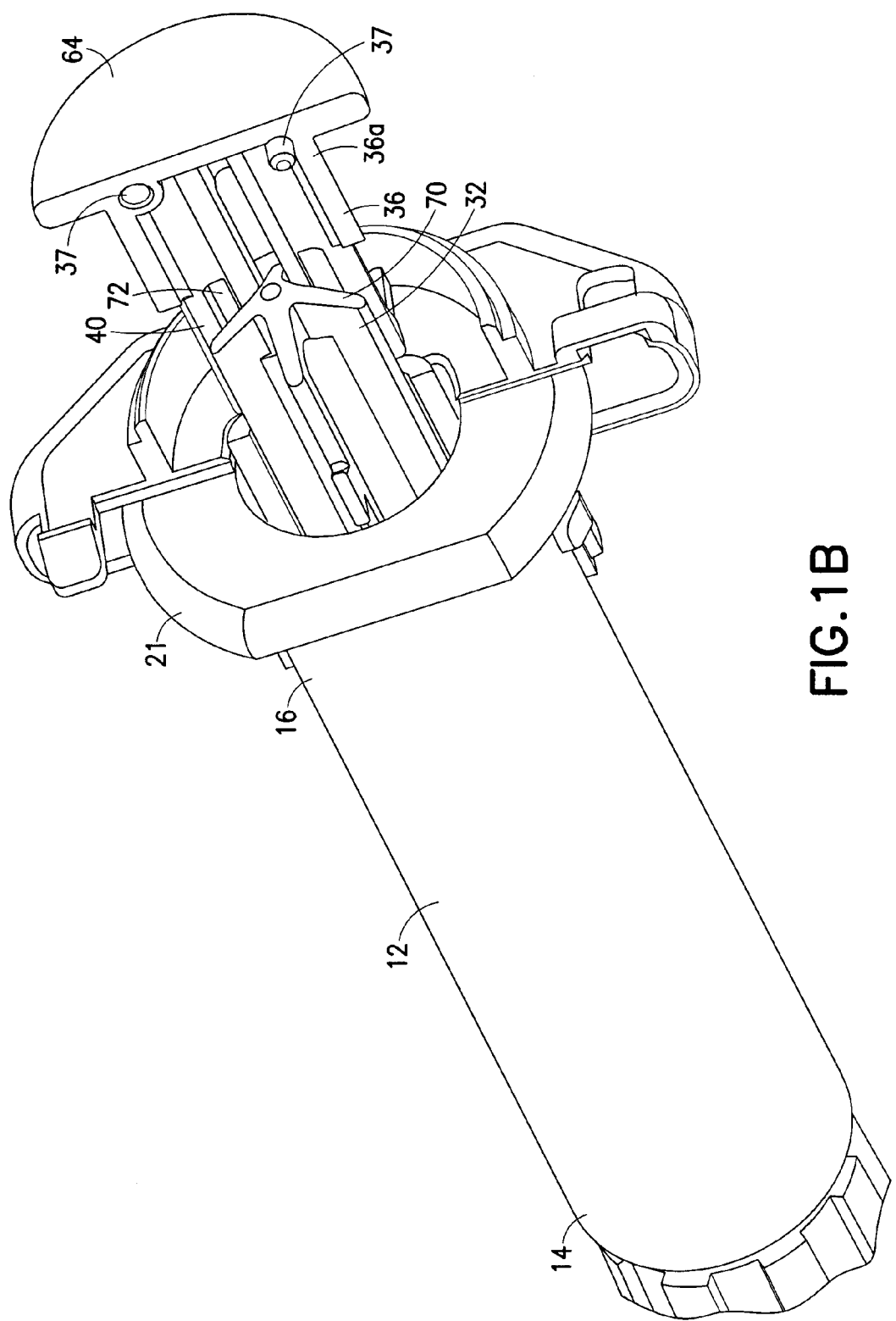
FIG. 1B is a front perspective view of the syringe assembly of FIG. 1 with the plunger rod in a collapsed position having a portion of the outer member removed in accordance with an embodiment of the present invention.
Figure 2A:
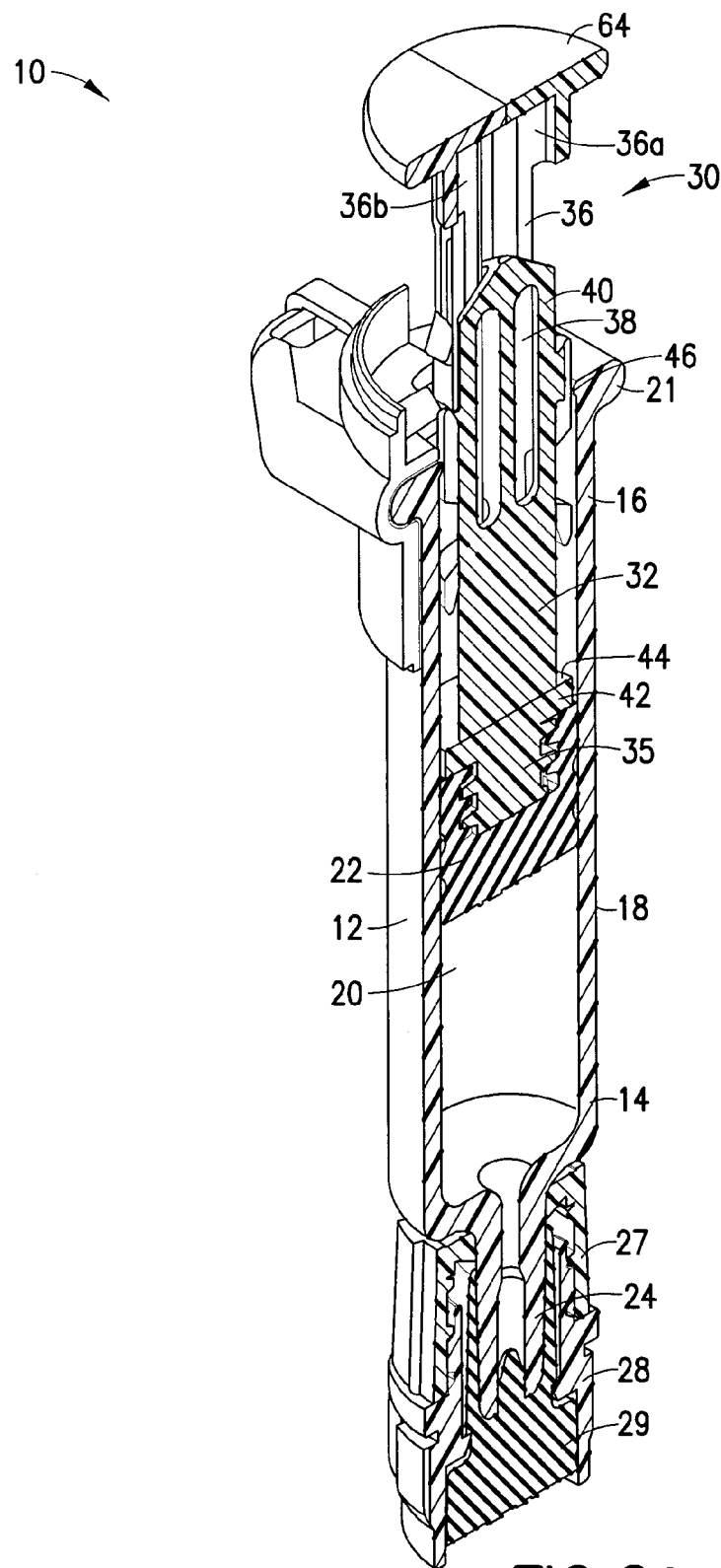
FIG. 2A is a cross-sectional perspective view of the syringe assembly taken along line IIA-IIA of FIG. 1 in accordance with an embodiment of the present invention.
Figure 2B:
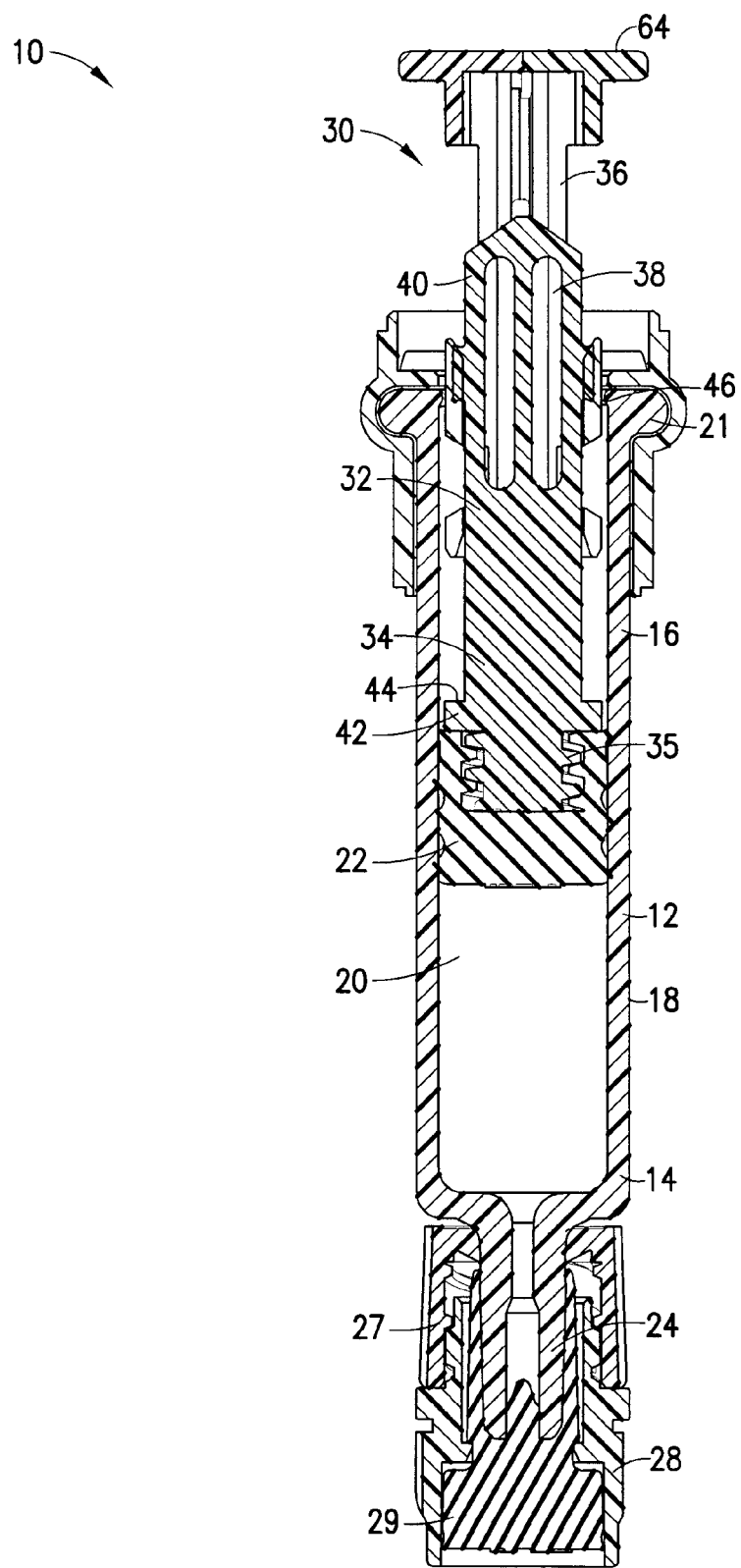
FIG. 2B is a cross-sectional plan view of the syringe assembly of FIG. 1 in accordance with an embodiment of the present invention.

With continuing reference to FIGS. 1, 1A-1B, 2A-2B, 3, 4A-4B, and 5A-5B, the syringe assembly includes a plunger rod, generally indicated as 30, for controlling movement of the stopper 22 through the syringe barrel 12 to either expel the syringe contents of a pre-filled type of syringe assembly 10 or, depending upon the desired use of the syringe assembly, to aspirate or withdraw a fluid into the syringe barrel 12. The plunger rod 30 includes an inner member 32 including a distal end 34 secured to the stopper 22 and an outer member 36 mounted for telescopic movement with respect to the inner member 32. It can be appreciated that the distal end 34 of the inner member 32 can include a mechanical attachment member 35 for securing the inner member 32 to the stopper. As shown in FIGS. 1, 1A-1B, 2A-2B, and 3, the outer member 36 can include a portion 38 for encompassing a portion 40 of the inner member 32. The plunger rod 30 is transitionable from a collapsed pre-use position, as shown in FIG. 1, to an extended ready-to-use position, as shown in FIG. 1A. According to one design, the outer member 36 can include a first part 36a and a second part 36b which can be mechanically joined together, such as by a snap member 37, about the inner member 32.

The plunger rod 30 can include a thumb press portion 64 or any other type of well-known member, upon which a user can apply a distally directed force to cause the plunger rod 30 to move the stopper 22, disposed within the syringe barrel 12, toward the distal end 14 of the syringe barrel 12 to expel the syringe contents during operation of the syringe assembly 10. This thumb press portion 64 can include a roughened or serrated surface, as is known in the art, to provide a frictional surface for assisting the user in movement or actuation of the plunger rod.

The syringe assembly 10 further includes at least one stop member 42 configured for cooperation with a portion of the syringe barrel 12 upon proximal movement of the outer member 36 with respect to the inner member 32 in a direction away from the first or distal end 14 of the syringe barrel 12 to limit the outward travel OT, shown in FIG. 1A, of the plunger rod 30 from the syringe barrel 12. The stop member 42 prevents pull-out of the plunger rod 30 from the syringe barrel 12. In other words, the stop member 42 prevents an inadvertent removal of the plunger rod 30 from the syringe assembly 10 upon the application of a proximal force PF, as shown in FIG. 5A, to extend the outer member 36 with respect to the inner member 32.

According to the configuration shown in FIGS. 1, 1A-1B, 2A-2B, 3, 4A-4B, and 5A-5B, the stop member 42 can comprise a laterally extending member 44 positioned at the distal end 34 of the inner member 32. This laterally extending member 44 extends in a lateral direction with respect to a longitudinal centerline L of the syringe barrel, as shown in FIG. 3, and is configured to cooperate with an internal portion 46 of the syringe barrel flange 21 to limit the outward travel OT of the plunger rod 30 from the syringe assembly 10 upon extension of the plunger rod 30 to the ready-to-use position.

Figure 5A:
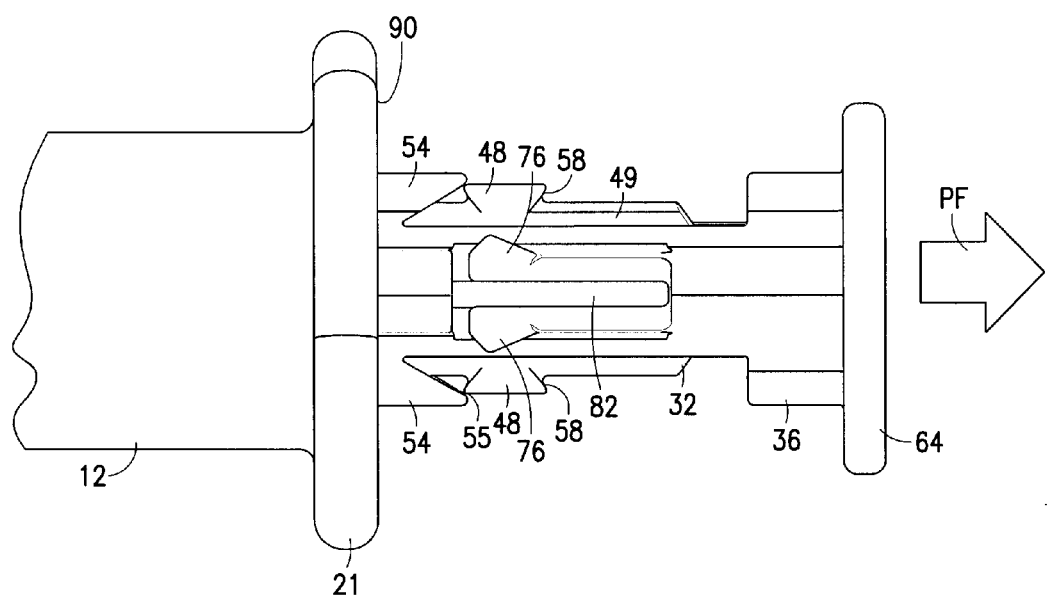
FIG. 5A is a side elevation view of the plunger rod assembly of the syringe assembly of FIG. 4A showing a proximal force being applied to the plunger rod in accordance with an embodiment of the present invention.

With particular reference to FIGS. 4A-4B and 5A-5B, the inner member 32 can include a locking member 48 for cooperating with an aperture 50 in the outer member 36 for locking the outer member 36 to the inner member 32 in the extended position. The outer member 36 can include a pair of holding members, such as a distal holding member 52, and a proximal holding member 54 surrounding the aperture 50. The distal holding member 52 and proximal holding member 54 can extend about the outer diameter of the outer member 36 in a lateral direction with respect to the longitudinal length L of the syringe assembly 10 and can have any shape which allows them to move throughout the syringe barrel 12 and which can adequately trap the locking member 48 when the outer member 36 is in the extended ready-to-use position. As shown in FIG. 5A, the proximal holding member 54 can have a configuration and a cooperating surface 55 that can receive the locking member 48 and allow the proximal holding member 54 to ride over the locking member 48 upon the application of the proximal force PF to the outer member 36 to extend the outer member 36 with respect to the inner member 32. Also, the locking member 48 can be mounted at the end of a flexible member 49, so that the locking member 48 flexes via the flexible member 49 in an inward direction with respect to the longitudinal centerline L of the syringe assembly 10 during extension of the outer member 36.

Figure 5B:
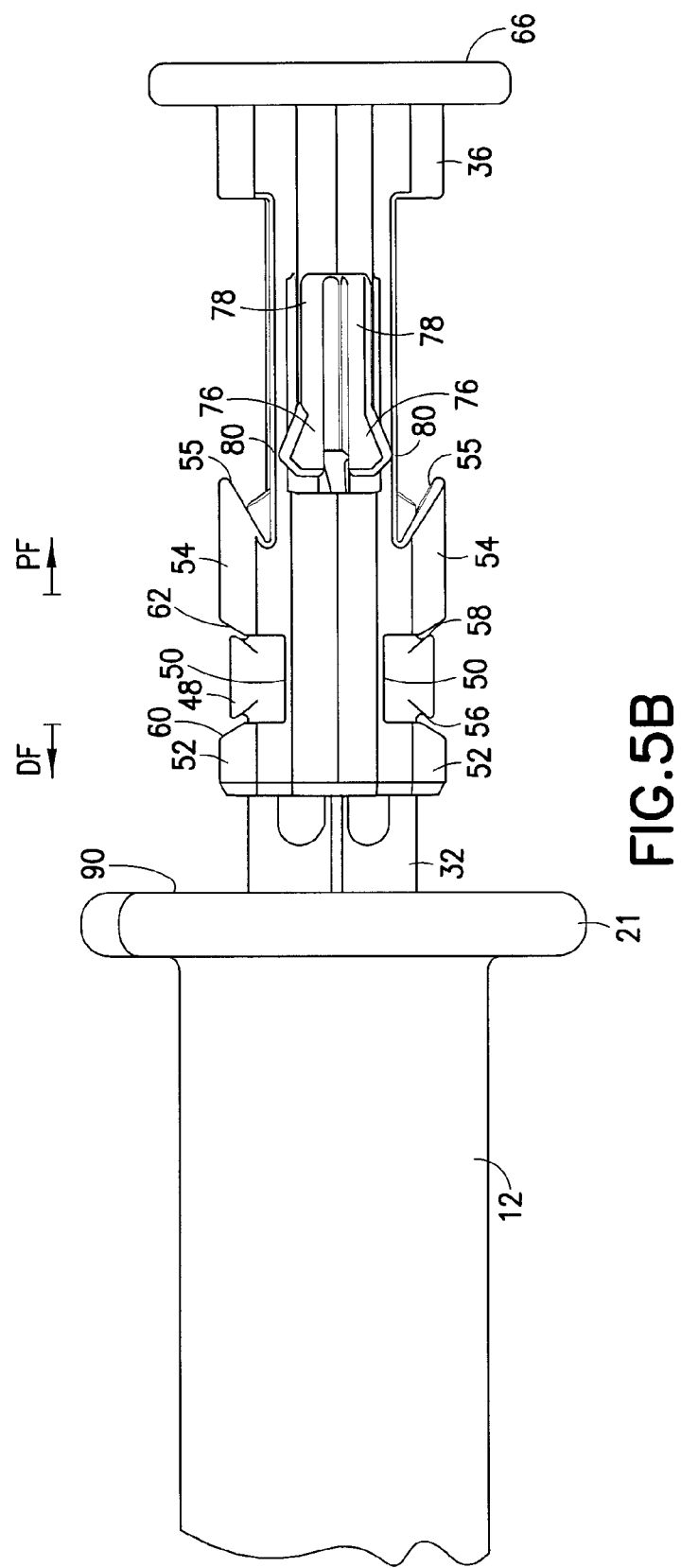
FIG. 5B is a side elevation view of the plunger rod assembly of the syringe assembly of FIG. 5A with the plunger rod in the extended position in accordance with an embodiment of the present invention.

The locking member 48 can include a pair of reverse bevel surfaces 56, 58 for cooperating with corresponding bevel surfaces 60, 62 on the pair of holding members 52, 54 to maintain the outer member 36 in the extended and locked position upon the application of either a distal force DF or a proximal force PF applied to the outer member 36, as shown in FIG. 5B.

According to one design, as shown in FIG. 1B, the inner member 32 can include a substantially X-shaped profile 70 configured for engagement with a corresponding substantially X-shaped opening 72 within the outer member 36. Although the drawings show an X-shaped profile, it can be appreciated that the inner member 32 and the outer member 36 can have any multi-lobe or any other type of configuration known in the art which allows for adequate telescoping of the outer member 36 with respect to the inner member 32.

With continuing reference to FIGS. 4A-4B and 5A-5B, the syringe assembly 10 can also include at least one detent 76 associated with the outer member 36 which is configured to cooperate with the syringe barrel 12 to limit movement of the outer member 36 into the syringe barrel 12 upon an application of a distally directed force to the plunger rod 30. This particular feature would prevent the application of a partial dose of a pre-filled syringe, should a distal force be applied to the plunger rod 30 prior to extension of the outer member 36. According to one embodiment, this detent 76 can comprise a flex finger 78 having a ramped portion 80 at one end thereof that prevents the application of a partial dose from a pre-filled syringe, as it limits or prevents the depression of the outer member 36 into the syringe barrel 12 prior to the desired use of the syringe assembly, i.e., until the extension of the outer member 36 with respect to the inner member 32. In operation and with particular reference to FIGS. 4A-4B and 5A, when the outer member 36 is in the collapsed position, a sidewall portion 82 of the inner member 32 supports or applies a supporting surface against the detent 76 and, should a distally directed force be applied to the plunger rod 30, the ramped portion 80 will engage against a top surface 90 of the flange 21 of the syringe barrel 12 to prevent movement of the plunger rod 30 into the syringe barrel 12 and to prevent the application of a partial dose of the syringe contents. Once the outer member 36 is extended with respect to the inner member 32, as shown in FIG. 5B, the sidewall portion 82 of the inner member 32 no longer provides a supporting surface against the detent 76. This will allow the flex finger 78 to flex inward with respect to the longitudinal centerline L of the syringe assembly 10. Accordingly, the application of a distally directed force to the plunger rod 30 to expel the syringe contents will cause the plunger rod 30 to move into the syringe barrel 12 and, when the ramped portion 80 of the detent 76 contacts the top surface 90 of the flange 21, the flex member 78 can flex in an inward direction to allow the outer member 36 to enter into the syringe barrel 12.

Reference is now made to FIGS. 6A-6B and 7A-7B which depict a syringe assembly according to a further embodiment of the present invention, generally indicated as 100, which can also be adapted for the dispensing and delivery of a fluid. The syringe assembly 100 is similar to syringe assembly 10, as discussed in detail above and includes a first or distal end 114, a second or proximal end 116, and a sidewall 118 extending between the distal end 114 and proximal end 116 defining an interior chamber 120 of a syringe barrel 112. A stopper 122 is disposed within the chamber 120 of the syringe barrel 112. The syringe barrel 112 may include an outwardly extending flange 121 about at least a portion of the proximal end 116. The flange 121 may be configured for easy grasping by a medical practitioner. The syringe assembly 100 can also include a tip cap 128.

Figure 6A:
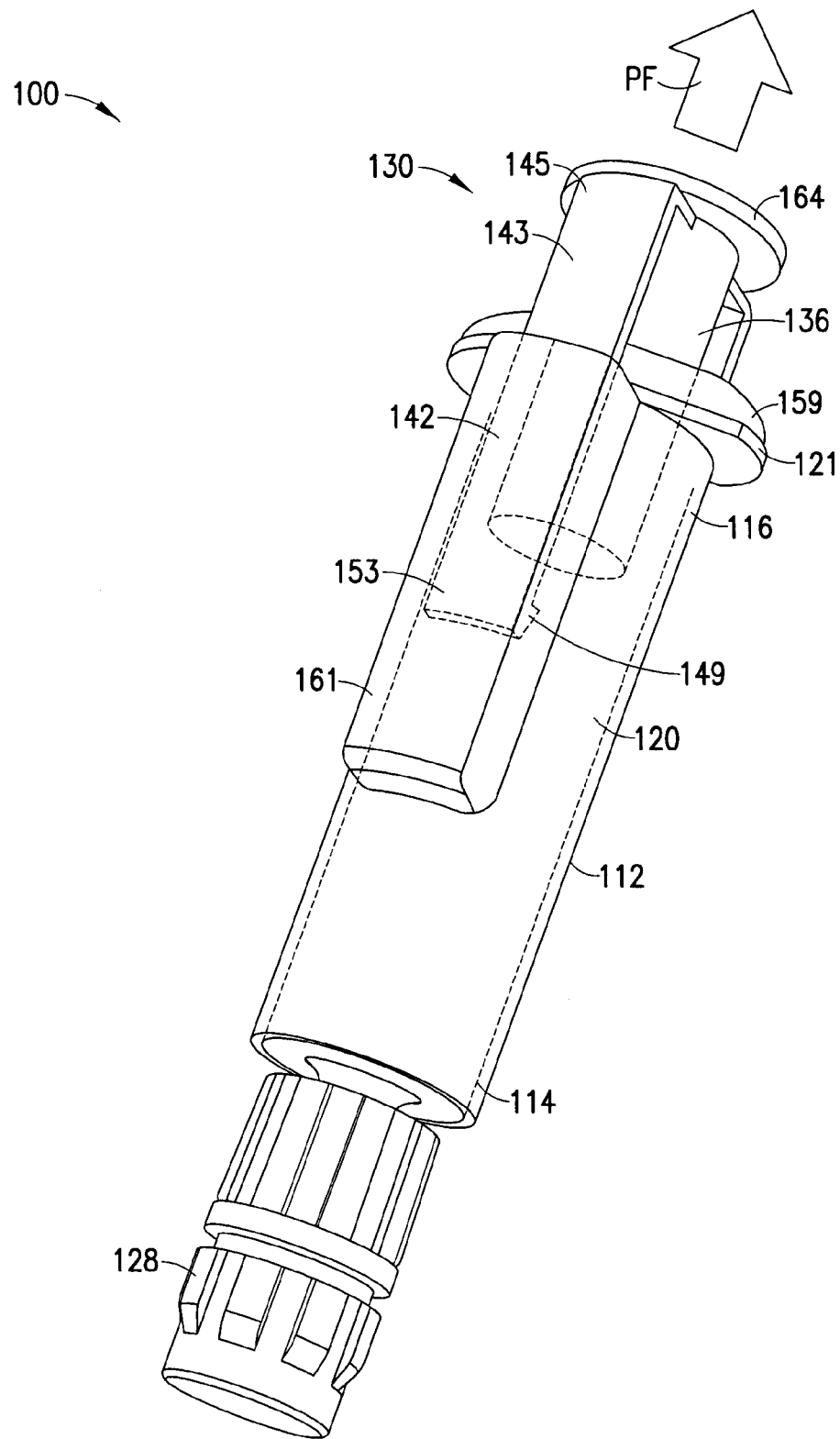
FIG. 6A is a front perspective view of a syringe assembly having a telescopic plunger rod in a collapsed position in accordance with an embodiment of the present invention.
Figure 6B:
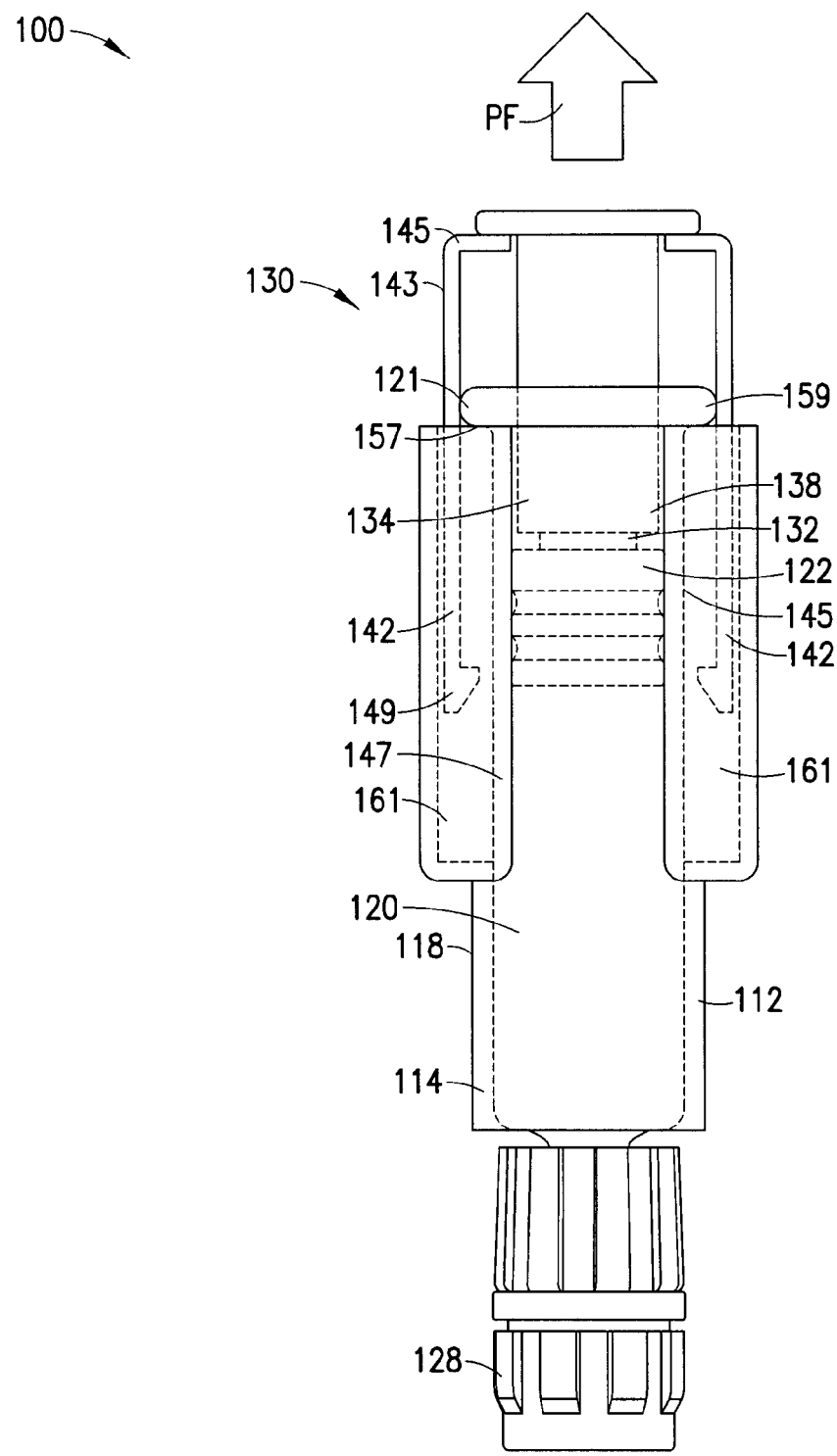
FIG. 6B is a side elevation view of the syringe assembly of FIG. 6A in accordance with an embodiment of the present invention.
Figure 7A:
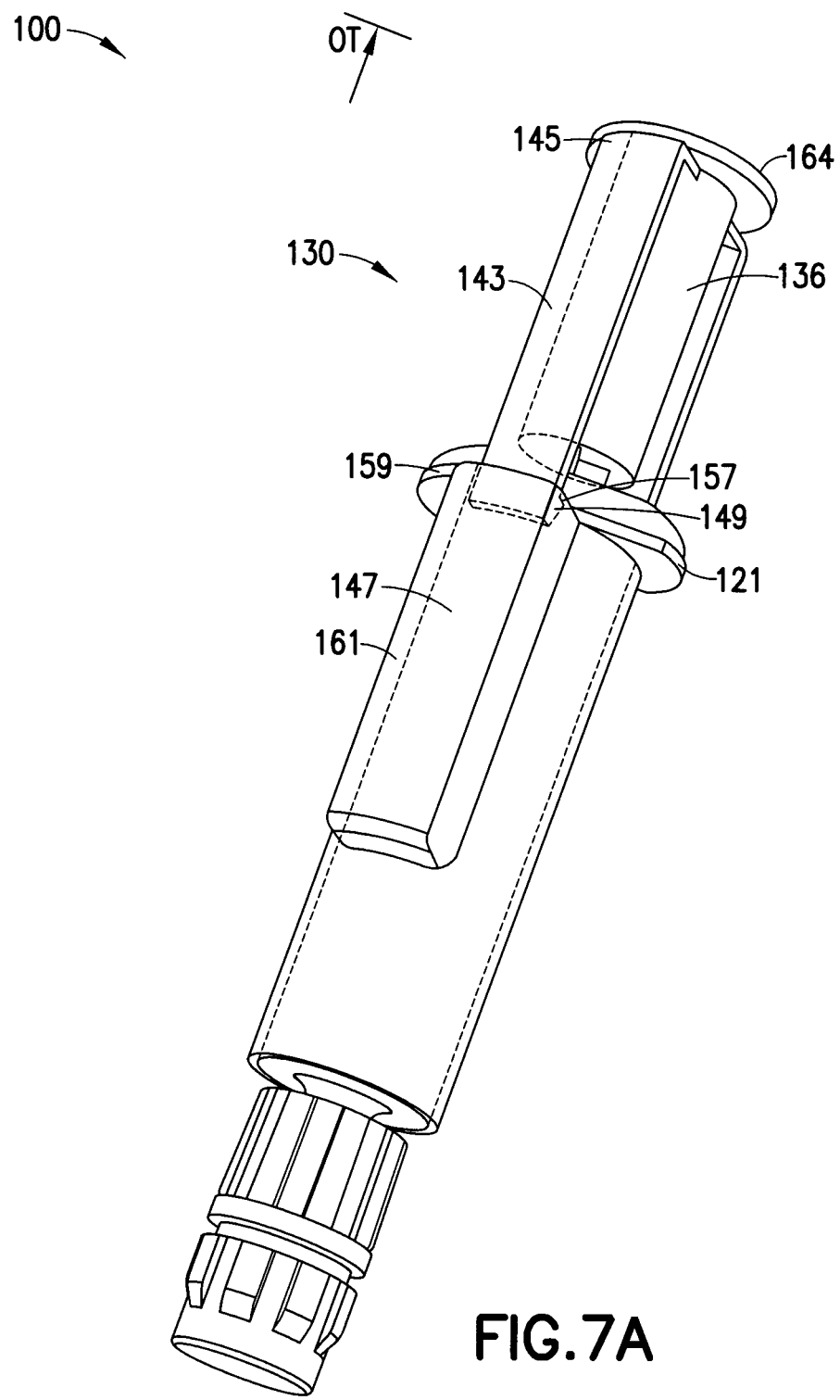
FIG. 7A is a front perspective view of the syringe assembly of FIG. 6A having a telescopic plunger rod in an extended position in accordance with an embodiment of the present invention.
Figure 7B:
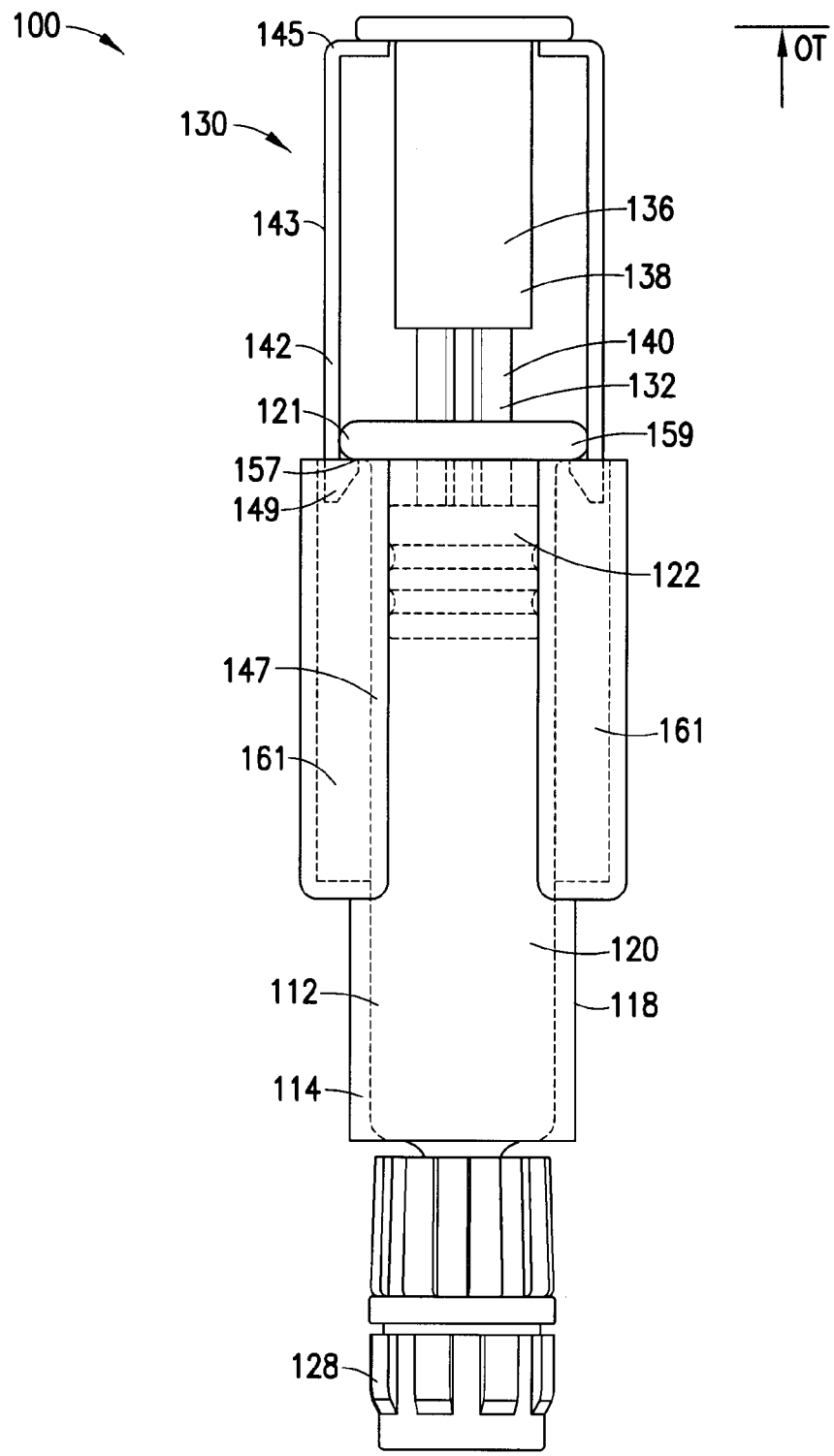
FIG. 7B is a side elevation view of the syringe assembly of FIG. 7A in accordance with another embodiment of the present invention.
Figure 8A:
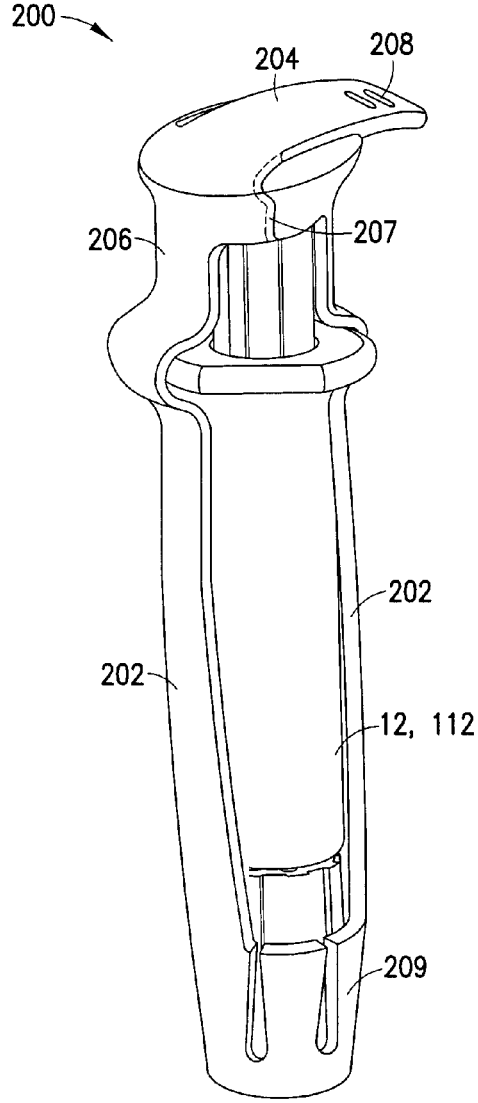
FIGS. 8A-8C are perspective side views of the syringe assembly of FIG. 1 illustrating the sequential operational steps for removing a packaging assembly in accordance with an embodiment of the present invention.
Figure 8B:
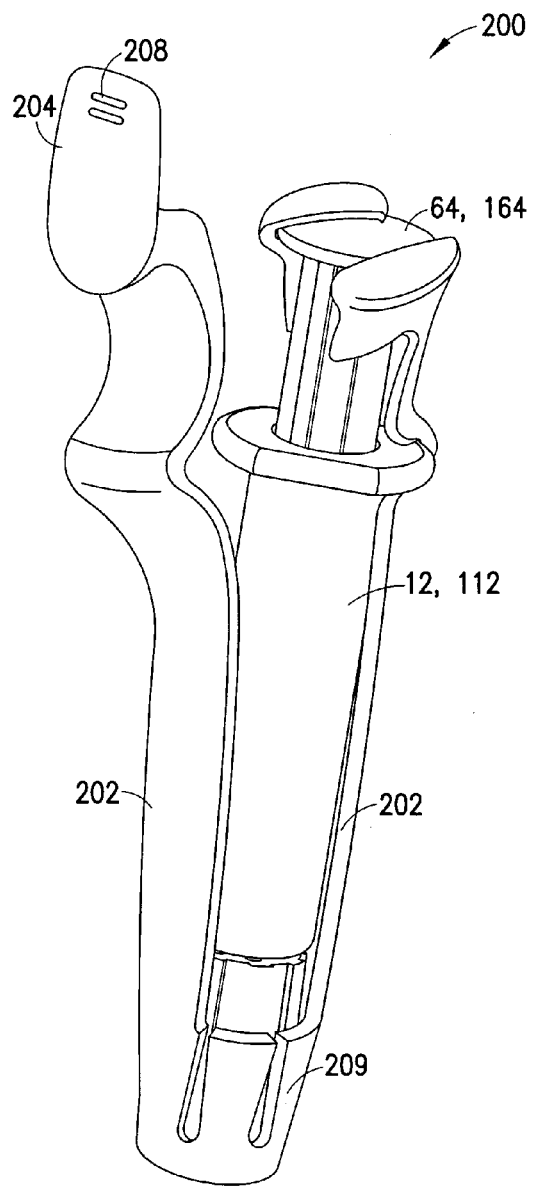
Figure 8C:
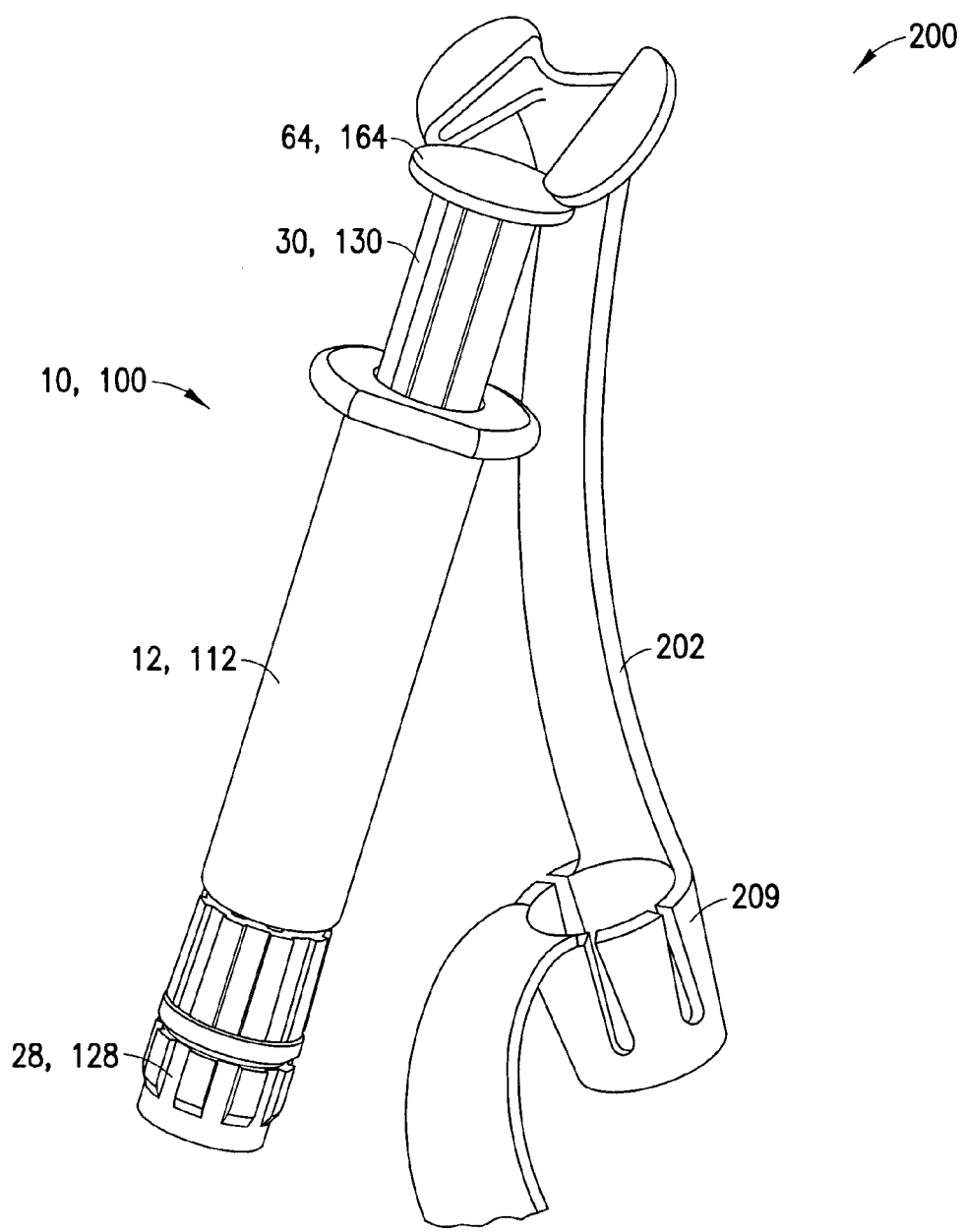

With continuing reference to FIGS. 6A-6B and 7A-7B, a plunger rod, generally indicated as 130, controls movement of the stopper 122 through the syringe barrel 112 to either expel the syringe contents of a pre-filled type of syringe assembly 100 or, depending upon the desired use of the syringe assembly, to aspirate or withdraw a fluid into the syringe barrel 112. The plunger rod 130 includes an inner member 132 including a distal end 134 secured to the stopper 122, and an outer member 136 mounted for telescopic movement with respect to the inner member 132. As shown in FIGS. 6B and 7B, the outer member 136 can include a portion 138 for encompassing a portion 140 of the inner member 132. The plunger rod 130 is transitionable from a collapsed pre-use position, as shown in FIGS. 6A-6B, to an extended ready-to-use position, as shown in FIGS. 7A-7B.

The syringe assembly 100 further includes at least one stop member 142 configured for cooperation with a portion of the syringe barrel 112 upon proximal movement of the outer member 136 with respect to the inner member 132 in a direction away from the first or distal end 114 of the syringe barrel 112 to limit the outward travel OT, shown in FIGS. 7A-7B, of the plunger rod 130 from the syringe barrel 112. The stop member 142 prevents pull-out of the plunger rod 130 from the syringe barrel 112. In other words, the stop member 142 prevents an inadvertent removal of the plunger rod 130 from the syringe assembly 100 upon the application of a proximal force PF, as shown in FIG. 5A, to extend the outer member 136 with respect to the inner member 132.

According to the configuration shown in FIGS. 6A-6B, the stop member 142 can comprise at least one longitudinally extending arm 143 having one end 145 associated with the outer member 136 wherein the longitudinally extending arm 143 extends along an outer portion 147 of the syringe barrel sidewall 118. The at least one longitudinally extending arm 143 can include an inwardly extending detent 149 at one end, such as a distal end 153 thereof, configured for contacting a bottom portion 157 of an outer portion 159 of the flange 121 of the syringe barrel 112 when the outer member 136 is in the extended ready-to-use position, as shown in FIGS. 7A-7B, for limiting the outward travel of the outer member 136. According to one design, the at least one longitudinally extending arm 143 can comprise a pair of arms, each of the arms 143 including the inwardly extending detent 149 configured for contacting the bottom portion 157 of the outer portion 159 of the flange 121 of the syringe barrel 112. In this configuration, the syringe barrel 112 can include at least one or a pair of pockets 161 for enclosing the longitudinally extending arms 143 when the outer member 136 is in the collapsed pre-use position. The at least one or pair of pockets 161 cooperate with the outer portion 159 of the flange 121 of the syringe barrel 112 to position and hold the detent 149 in contact with the outer portion 159 of the flange 121.

Reference is now made to FIGS. 8A-8C which depict a packaging assembly, generally indicated as 200, and the sequential operational steps for removing the packaging assembly 200 from the syringe assembly 10, 100 in accordance with an embodiment of the present invention. The packaging assembly 200 includes a molded cover 202 configured for placement about a portion of the syringe barrel 12, 112, the plunger rod 30, 130, and the tip cap 28, 128. A tear tab 204 can be associated with one end 206 of the molded cover 202. The tear tab 204 is configured, such as by the inclusion of a frangible portion 207, to facilitate removal of the molded cover 202 from the syringe assembly 12, 112 and can be positioned adjacent a top surface or thumb press 64, 164 of the plunger rod 30, 130. The tear tab 204 can include a roughened or serrated surface 208, as is known in the art, to provide a frictional surface for assisting the user in grasping of the tear tab 204. The cover 202 is configured for placement about the syringe assembly 10, 100 to constrain the plunger rod 30, 130 from inadvertent extension and to prevent tampering of the syringe assembly 10, 110. The cover 202 can include an end portion 209 configured to fit about the tip cap 28, 128 to prevent its removal from the syringe assembly 10, 100. The cover 202 can also be placed at a location about the syringe barrel 12, 112 to prevent damage to the syringe barrel 12, 112 during packaging, shipment, and handling.

It can be appreciated that each of the syringe assembly embodiments disclosed above result in a syringe assembly having a reduced footprint which is desirable in the packaging of the syringe assemblies as it requires less packaging. This reduced footprint provides for syringe assemblies having consistently sized profiles which allow for easy stacking and require less storage space, both of these features being desirable in a controlled storage environment.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

The invention claimed is:

1. A syringe assembly comprising:
   a syringe barrel having a first end, a second end, and a sidewall extending between the first end and the second end defining a chamber;
   a stopper disposed within the chamber of the syringe barrel;
   a plunger rod having both an inner member engaged with the stopper and an outer member adapted for telescopic movement with respect to the inner member, wherein the plunger rod is transitionable from a collapsed position in which a portion of the inner member is nested within the outer member, to an extended position in which the same portion of the inner member extends outside the outer member; and
   at least one stop member located on the inner member of the plunger rod configured for cooperation with a portion of the syringe barrel upon relative movement of the outer member with respect to the inner member to limit the outward travel of the plunger rod from the syringe barrel,
   wherein the outer member comprises at least one detent having at least one flexible finger, the detent configured to cooperate with the syringe barrel to limit movement of the outer member into the syringe barrel upon the application of a distally directed force to the plunger rod prior to the plunger rod transitioning to the extended position.

2. The syringe assembly of claim 1, wherein the at least one stop member limits pull-out of the plunger rod from the syringe barrel.

3. The syringe assembly of claim 1, wherein the at least one stop member comprises a laterally extending member positioned at a distal end of the inner member.

4. The syringe assembly of claim 3, wherein the laterally extending member is configured to cooperate with an internal portion of a syringe barrel flange to limit the outward travel of the plunger rod from the syringe assembly upon extension of the plunger rod to the extended position.

5. The syringe assembly of claim 4, wherein the inner member comprises a locking member for cooperating with an aperture in the outer member for locking the outer member to the inner member in the extended position.

6. The syringe assembly of claim 5, wherein the outer member comprises a pair of holding members surrounding the aperture and the locking member comprises a pair of reverse bevels for cooperating with the pair of holding members to maintain the outer member in the extended position upon the application of a distal force and a proximal force applied to the outer member.

7. The syringe assembly of claim 1, wherein the inner member comprises a substantially X-shaped profile configured for engagement with a corresponding substantially X-shaped opening within the outer member.

8. The syringe assembly of claim 1, further comprising a molded cover having a tear tab for removal of the cover, wherein the cover is configured to constrain the plunger rod from inadvertent transition to the extended position.

9. The syringe assembly of claim 1, further comprising a medication or drug disposed within the syringe barrel.

10. The syringe assembly of claim 1,
wherein, when the outer member is in the collapsed position, a portion of the inner member contacts at least one flexible finger such that the at least one flexible finger is held in a stressed state wherein, if a distally directed force is applied to the plunger rod, the at least one flexible finger engages an upper portion of the syringe barrel and thereby limits the movement of the outer member in the distal direction, and
wherein, when the outer member is in the extended position, the at least one flexible finger is allowed to enter a relaxed state wherein the at least one flexible finger no longer limits the movement of the outer member in the distal direction.

11. The syringe assembly of claim 10, wherein the at least one flexible finger comprises a ramped portion which, when the outer member is in the collapsed position, engages a sidewall portion of the inner member and thereby forces the at least one flexible finger to be in the stressed state.

12. A telescopic plunger rod assembly comprising:
a plunger rod for use with a syringe assembly, the plunger rod comprising both:
an inner member having a distal end configured for being secured to a stopper located within a syringe barrel, and
an outer member having an open portion configured for telescopically engaging a portion of the inner member, wherein the outer member is integral with the plunger rod, wherein the plunger rod is transitionable from a collapsed position to an extended position; and
at least one stop member located on the inner member of the plunger rod configured for cooperation with a portion of the syringe barrel to limit the outward travel of the outer member from the syringe barrel upon transition of the plunger rod to the extended position, wherein the outer member comprises at least one detent having at least one flexible finger, the detent configured to cooperate with the syringe barrel to limit movement of the outer member into the syringe barrel upon the application of a distally directed force to the plunger rod prior to the plunger rod transitioning to the extended position.

13. The telescopic plunger rod assembly of claim 12, wherein the at least one stop member comprises a laterally extending member positioned at the distal end of the inner member and configured to cooperate with an internal portion of a syringe barrel flange to limit the outward travel of the plunger rod from the syringe assembly upon extension of the plunger rod to the extended position.

14. The telescopic plunger rod assembly of claim 13, wherein the inner member comprises a locking member configured for cooperating with an aperture in the outer member for locking the outer member to the inner member in the extended position.

15. The telescopic plunger rod assembly of claim 14, wherein the inner member comprises a substantially X-shaped profile configured for engagement with a corresponding substantially X-shaped opening within the outer member.

16. The telescopic plunger rod assembly of claim 12,
wherein, when the outer member is in the collapsed position, a portion of the inner member contacts the at least one flexible finger such that the at least one flexible finger is held in a stressed state wherein, if a distally directed force is applied to the plunger rod, the at least one flexible finger engages an upper portion of the syringe barrel and thereby limits the movement of the outer member in the distal direction, and
wherein, when the outer member is in the extended position, the at least one flexible finger is allowed to enter a relaxed state wherein the at least one flexible finger no longer limits the movement of the outer member in the distal direction.

17. The telescopic plunger rod assembly of claim 16, wherein the at least one flexible finger comprises a ramped portion which, when the outer member is in the collapsed position, engages a sidewall portion of the inner member and thereby forces the at least one flexible finger to be in the stressed state.

* * * * *